United States Patent [19]

Peralta

[11] 4,069,587

[45] Jan. 24, 1978

[54] DENTAL HANDPIECE CONTROL APPARATUS

[75] Inventor: Michael A. Peralta, Miami, Fla.

[73] Assignee: Simplair Systems, Inc., Hollywood, Fla.

[21] Appl. No.: 623,618

[22] Filed: Oct. 20, 1975

[51] Int. Cl.$^2$ ............................................. A61C 19/02
[52] U.S. Cl. ...................................................... 32/22
[58] Field of Search ....................... 32/27, 22; 137/842

[56] References Cited

U.S. PATENT DOCUMENTS

| | | | |
|---|---|---|---|
| 3,516,439 | 6/1970 | Hicks et al. | 137/842 |
| 3,638,310 | 1/1972 | Austin | 32/22 |
| 3,672,059 | 6/1972 | Booth | 32/22 |
| 3,817,246 | 6/1974 | Weigl | 137/842 |
| 3,904,841 | 9/1975 | Swatman | 32/22 |

Primary Examiner—Robert Peshock
Attorney, Agent, or Firm—Blum, Moscovitz, Friedman & Kaplan

[57] ABSTRACT

In the present apparatus, the removal of a dental handpiece from its holder opens a pilot-operated valve for supplying air or both air and water to the handpiece in conjunction with the usual foot pedal-operated valve.

Preferably, the holder has aligned, narrow air passages on opposite sides of a recess which receives the handpiece, and the handpiece blocks these passages when it is in the holder. Upon removal of the handpiece, the flow of air from one of these passages across the recess and into the other passage supplies the pilot pressure for opening the pilot-operated valve. The pilot-operated valve may be separate from the holder or contained within it.

In another embodiment, the holder has a reciprocable valve member controlling the application of pilot pressure to the pilot-operated valve. This valve member is depressed to a closed position by the handpiece when the latter is in the holder and is biased to an open position when the handpiece is removed from the holder.

32 Claims, 18 Drawing Figures

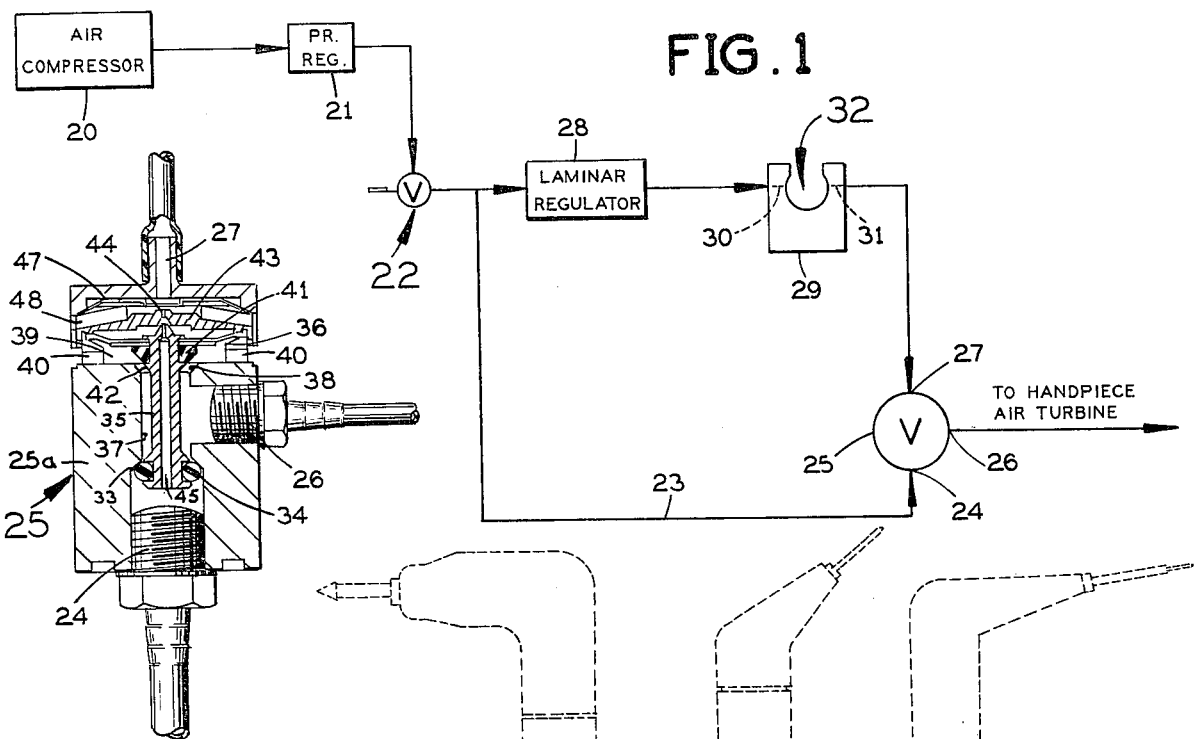
FIG. 1
FIG. 3
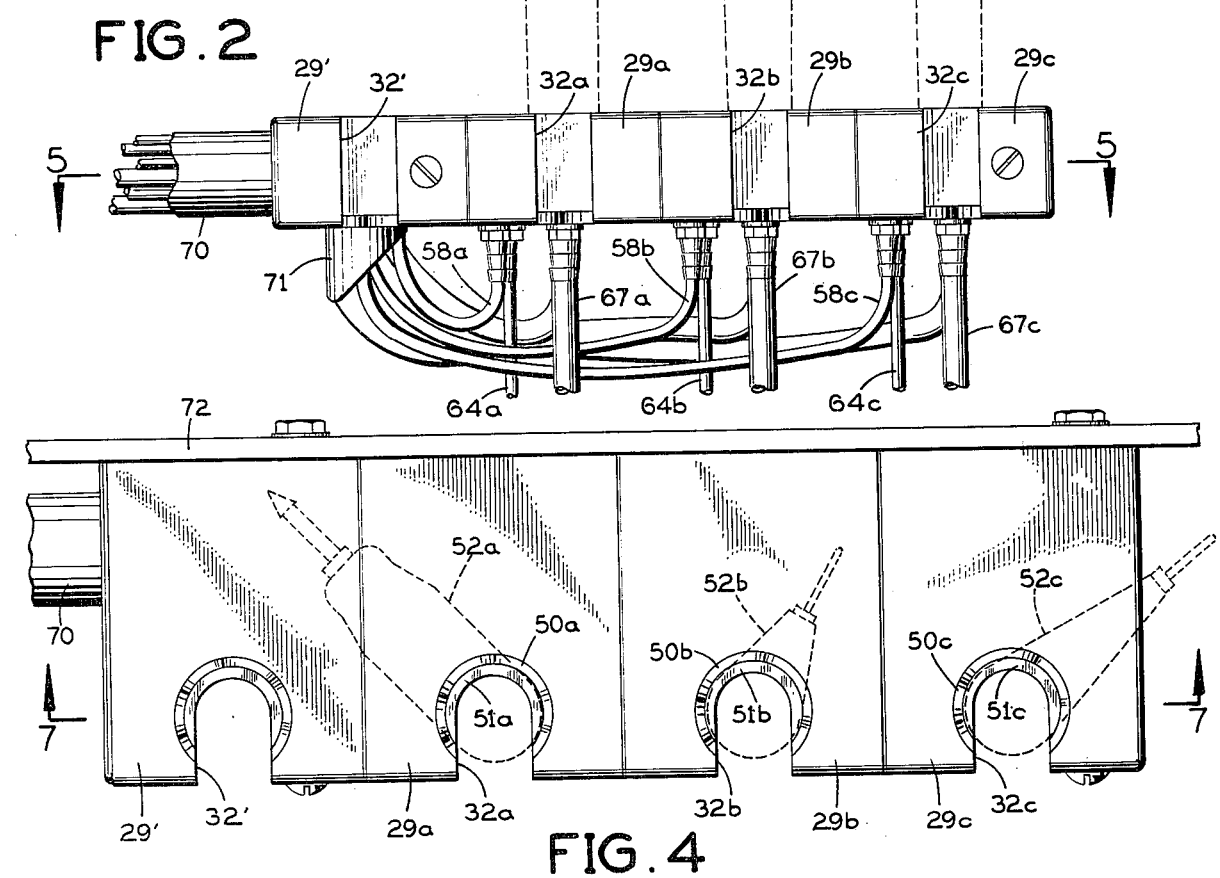
FIG. 2
FIG. 4

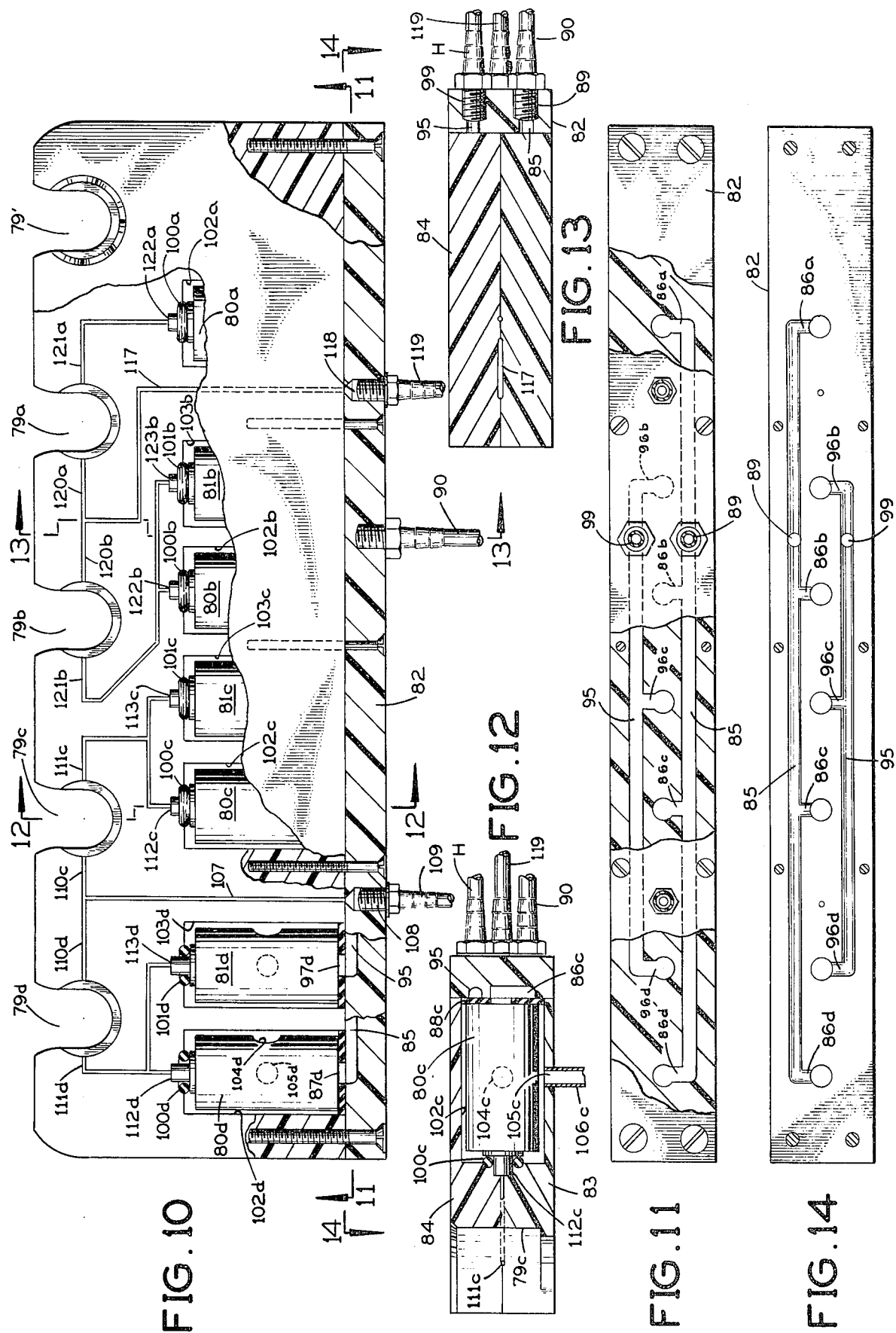

DENTAL HANDPIECE CONTROL APPARATUS

BACKGROUND OF THE INVENTION

Conventional dental drills are operated by air turbines. High speed dental drills also usually have provision for discharging a stream of water onto the patient's tooth. Various arrangements have been adopted for enabling the dentist to selectively control the supply of air, or air and water, to the drill. Typically, such control arrangements have involved a combination of electrtical control devices, and their associated wiring, and pneumatic, or pneumatic and hydraulic control devices, along with their associated hoses and fittings. In general, such prior control arrangements have been excessively complex, expensive and somewhat unwieldy and difficult to repair because of the presence of both electrical and pneumatic, or pneumatic and hydraulic, control devices and conduits.

SUMMARY OF THE INVENTION

The present invention is directed to a novel and improved apparatus for use with dental handpieces, such as drills, which require air or both air and water for their operation. In the present apparatus, the desired control functions are performed entirely pneumatically and there is no necessity to provide electrical control devices and their associated wiring.

In accordance with the present invention, a fluidic valve is controlled in accordance with whether the handpiece is in or out of its holder. When the handpiece is removed from its holder, this valve supplies pilot pressure to open a pilot-operated valve that is connected to supply air or water to the handpiece.

In the preferred embodiment, the handpiece itself is part of the aforementioned fluidic valve. The holder has a pair of aligned, narrow air passages on opposite sides of a recess in which the handpiece normally is seated, thereby blocking these air passages. When the handpiece is removed, air is discharged from one of these passages across the recess and into the other passage for supplying pilot pressure to open the pilot-operated valve.

In another embodiment, the handpiece mechanically operates the fluidic valve, keeping this valve closed when the handpiece is in its holder and permitting it to open when the handpiece is removed from its holder.

A principal object of this invention is to provide a novel and improved dental apparatus which enables a dental handpiece to be completely controlled fluidically.

Another object of this invention is to provide such an apparatus which avoids the undue expense and complexity of previous control arrangements in dental apparatus which were in part electrically operated.

Another object of this invention is to provide such an apparatus which is compatible with conventional control devices, such as foot-operated valves, used previously to control the supply of air, or both air and water, to dental handpieces.

Further objects and advantages of the present invention will become apparent from the following detailed description of three presently-preferred embodiments thereof, which are illustrated in the accompanying drawings in which:

FIG. 1 is a block diagram showing schematically the constituent parts of a system embodying the present apparatus;

FIG. 2 is a front elevational view of the holder for dental handpieces in this apparatus;

FIG. 3 is a vertical section through a known type of pilot-operated valve whose operation is controlled from the handpiece holder in the present apparatus;

FIG. 4 is top plan view of this handpiece holder;

FIG. 10 is a top plan view, with parts broken away for clarity, showing a dental handpiece holder which contains the pilot-operated valves in accordance with a second embodiment of this invention;

FIG. 11 is a vertical section, taken along the line 11—11 in FIG. 10, through the back piece of the holder;

FIG. 12 is a vertical cross-section taken along the line 12—12 in FIG. 10;

FIG. 13 is a vertical cross-section taken along the line 13—13 in FIG. 10;

FIG. 14 is a vertical longitudinal section taken along the line 14—14 in FIG. 10 at the front of the back piece of the holder;

Figure 5:
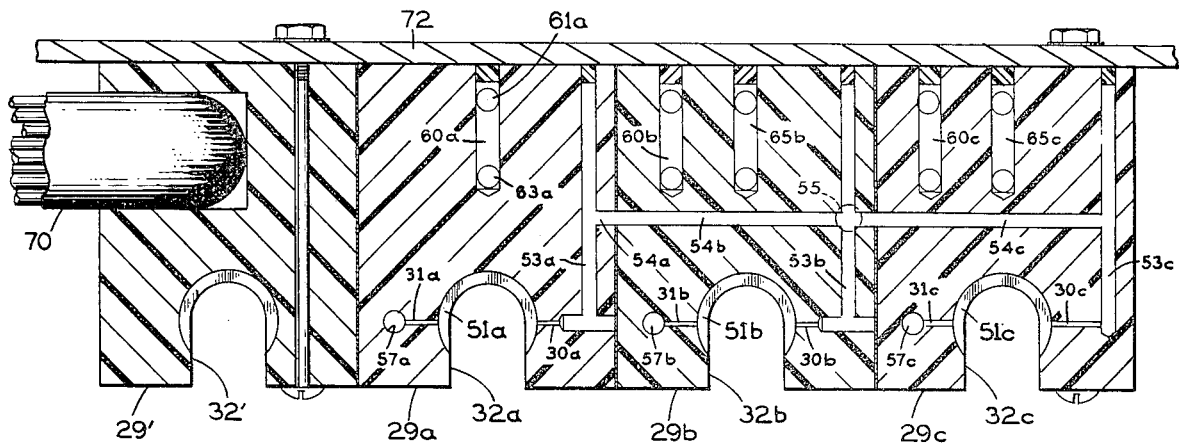
FIG. 5 is a longitudinal horizontal section through the handpiece holder, taken along the line 5—5 in FIG. 2.

Before explaining the disclosed embodiments of the present invention in detail, it is to be understood that the invention is not limited in its application to the details of the particular arrangements shown, since the invention is capable of other embodiments. Also, the terminology used herein is for the purpose of description and not of limitation.

Referring first to the schematic block diagram of FIG. 1, the system illustrated there is intended to control the supply of pressurized air to a dental handpiece, such as a drill, which is operated by an air turbine. The handpiece and its air turbine are of known design, the details of which are not part of the present invention.

In this system an air compressor 20 is connected through a pressure regulator 21 to a foot-operated valve 22. These three components are of conventional design. Preferably, the air pressure at the outlet side of valve 22 is proportional to how far the foot pedal is depressed. Valve 22 is connected through a main outlet hose or line 23 to the main inlet 24 of a normally-closed, pilot-operated air valve 25 of known design, which is shown in detail in FIG. 3. This valve has a main outlet 26 leading to the air turbine in the dental handpiece.

In one practical embodiment, valve 25 is a "Miniamp 146-1" valve manufactured by Creative Automation Technology of Granby, Connecticut. Alternatively, valve 25 may be the "Model 2010" valve manufactured by Clippard Industries of Cincinnati, Ohio.

Valve 25 has a pilot pressure inlet port 27, the air pressure at which controls the opening and closing of this valve. This pilot pressure port 27 is connected to the outlet of the foot pedal-operated valve 22 through a laminar pressure regulator 28 of known design and aligned air jet passages in the holder 29 for this dental handpiece. These passages in the handpiece holder are indicated schematically at 30 and 31 in FIG. 1. They are located on opposite sides of a recess 32, open at the top and the front of the holder, in which the dental handpiece normally is seated.

When the handpiece is seated in holder 29, as described in detail hereinafter, its passages 30 and 31 are blocked by the handpiece and for this reason the valve-opening pilot pressure is not applied to the pilot pressure inlet port 27 of valve 25. Consequently, valve 25 will remain closed and the air turbine for this handpiece cannot operate.

When the handpiece is removed from its holder 29, this puts its air passages 30 and 31 in communication with each other across the air gap previously occupied by the handpiece. Therefore, if the foot pedal for valve 22 is depressed, pilot air pressure will be applied to pilot port 27 of valve 25 and the latter will be opened to connect its main inlet port 24 to its main outlet port 26 for operating the air turbine in the handpiece which has been removed from its holder.

Accordingly, it will be understood that in this system the air turbine for the handpiece is controlled jointly by the foot-operated valve 22 and by its own position with respect to its holder 29. This air turbine is turned on only if both of the following two conditions are met:
1. the foot pedal for valve 22 is depressed; and
2. the handpiece is removed from holder 29.

In effect, the handpiece and its holder 29 together constitute a manually-operated pneumatic valve which controls the application of pilot pressure to the pilot-operated valve 25.

Referring now to FIG. 3, the pilot-operated valve 25 has a cylindrical valve body 25a with a frusto-conical first valve seat 33 which faces down toward the main inlet port 24. An O-ring 34 of rubber-like material normally is seated on this valve seat to block the flow of pressurized air from the main inlet port 24 to the main outlet port 26. This O-ring is carried on the lower end of a hollow stem 35. The upper end of this stem is attached to a flexible and resilient first diaphragm 36 of rubber-like material.

The valve body 25a has a vertical air passage 37 extending up from the first valve seat 33 and connected to the main outlet port 26. The valve stem 35 extends up through this passage 37 and is spaced from the sidewall of this passage. At the upper end of passage 37, the valve body presents an upwardly-facing, frusto-conical second valve seat 38. Above this second valve seat 38 the valve body has an annular chamber 39 leading to several exhaust ports 40. An annular valve member 41 of rubber-like material is carried by the valve stem 35 between the bottom of diaphragm 36 and an upwardly-facing annular shoulder 42 on the valve stem. Valve member 41 is sealingly engageable with the second valve seat 38 when the valve stem 35 is displaced downward from the position shown in FIG. 3.

Above the diaphragm 36 the valve housing carries a rigid cross wall 43 formed with a small central opening 44. The valve stem 35 has a central longitudinal passageway 45 whose lower end is open to the main inlet port 24. This passageway has a reduced diameter opening at the upper end of the valve stem (above diaphragm 36) which is aligned vertically with the cross wall opening 44.

Above the cross wall 43 the valve body carries a flexible and resilient second diaphragm 47. The top face of diaphragm 47 is exposed to the air pressure at the pilot pressure inlet port 27. The diaphragm 47 has an inherent bias upward, as shown in FIG. 2, to a position in which it uncovers the central opening 44 in cross wall 43. The valve body has a plurality of exhaust ports 48 which communicate with the space between the bottom of diaphragm 47 and the top of cross wall 43.

In the absence of a predetermined air pressure at the pilot pressure inlet port 27, the various parts of valve 25 assume the positions shown in FIG. 3. The main outlet port 26 is connected to the exhaust ports 40 via the second valve seat 38. The longitudinal passageway 45 in valve stem 35 is connected to the exhaust ports 48 via the opening 44 in the cross wall 43. Therefore, if air pressure is supplied to the main inlet port 24 (by opening the foot pedal-operated valve 22 in FIG. 1), in the absence of pilot pressure at port 27 this supply of pressurized air will be vented to the atmosphere via the exhaust ports 48, and the O-ring 34 will remain seated on valve seat 33 to block the main inlet port 24 from the main outlet port 26.

Figure 9:
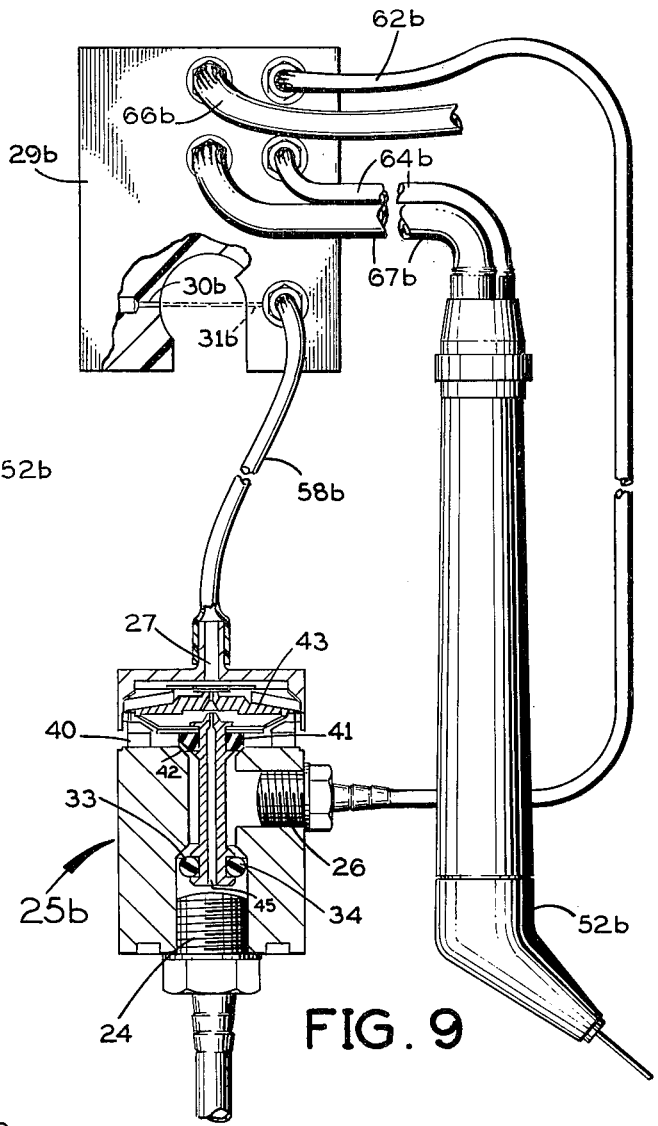
FIG. 9 is a view, partly in elevation and partly in section, showing one of the handpieces removed from its recess in the handpiece holder for opening the corresponding pilot-operated valve in the system.
Figure 15:
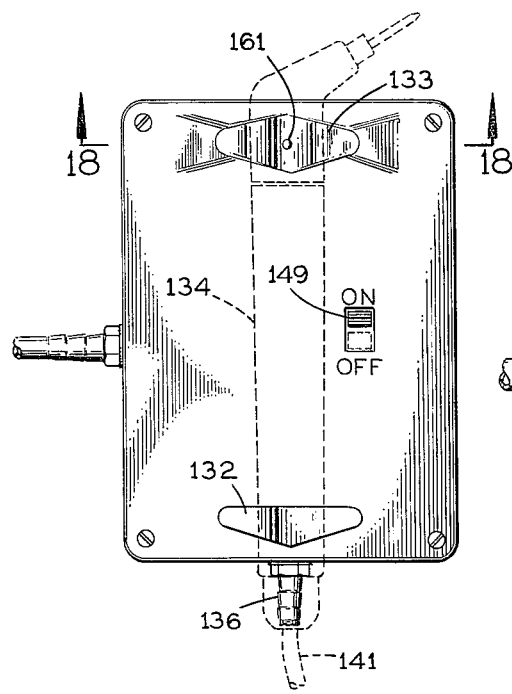
FIG. 15 is a top plan view of a dental handpiece holder in accordance with a third embodiment of this invention, with the handpiece itself shown in phantom.

However, when the pilot pressure port 27 receives pressurized air the various parts of the valve will move to the position shown in FIG. 9. As shown here, the diaphragm 47 is displaced downward by this pilot air pressure to a position in which it closes the central opening 44 in cross wall 43. Therefore, the pressurized air at the main inlet port 24 will be applied through the central passage 45 in valve stem 35 to the space between the bottom of cross wall 43 and the top of diaphragm 36, forcing the latter downward so as to displace the valve stem 35 down to the FIG. 9 position, in which the valve member 41 seats on the upwardly-facing valve seat 38 and the O-ring 34 is unseated from the downwardly-facing valve seat. Consequently, the main inlet port 24 now is connected to the main outlet port 26, the main inlet port 24 is blocked from the exhaust ports 48, and the main outlet port 26 is blocked from the exhaust ports 40.

While the system illustrated schematically in FIG. 1 is for just a single dental handpiece, in the typical situation the dentist will have a unitary assembly of holders for several handpieces. For example, as shown in FIGS. 2–7 the holder assembly is for four dental handpieces, two of which have both an air turbine and a water supply, one of which has an air turbine but no water supply, and one of which has neither an air turbine nor a water supply. The holder 29' for the latter is shown at the left end of the assembly in FIGS. 2–7. It is a simply a block having a U-shaped recess 32' for holding this handpiece, which may be a syringe S (FIG. 7).

Each of the other three holders in the assembly of FIGS. 2–7 functions in the manner outlined in the preceding general description of the system with reference to FIG. 1. These holders are designated 29a, 29b and 29c, from left to right in these Figures.

The generally U-shaped recess 32a in holder 29a has a chamfered top edge 50a (FIG. 7) and an inwardly extending, transverse shoulder 51a near its bottom end for supporting the corresponding dental handpiece 52a at its lower end. The air jet passages 30a and 31a on opposite sides of the handpiece-receiving recess 32a in this holder are located midway from top to bottom along this recess. These air jet passages extend horizontally and are aligned with each other on opposite sides of the recess 32a, so that when this recess is unobstructed a narrow jet of air can flow from passage 30a across the air gap and into passage 31a on the opposite side of the handpiece-receiving recess 31a.

In one pracitcal embodiment each passage 30a and 31a has a diameter within the range from 0.0035 to 0.0040 inch, and the distance across the recess 32a between these passages is 0.65625 (21/32) inch. The length of the air gap should be not more than twenty times the passage diameter in order to insure that the air jet discharged by passage 30a will enter passage 31a and produce sufficient pilot pressure therein for opening the pilot-operated valve. The regulated air pressure at the outlet side of the pressure regulator 21 in FIG. 1 preferably is within the range from 25 to 50 pounds per square inch, which is conventional for dental air compressors. The output pressure from the laminar flow regulator 28 preferably is about 0.5 pound per square inch.

Referring to FIG. 5, the air jet passage 30a is connected to the front end of a horizontal air supply passage 53a formed in this holder 29a. A transverse, horizontal air supply passage 54a intersects passage 53a and registers with a similar air passge 54b, which extends from side to side through the adjoining holder 29b immediately to the right of holder 29a. Passage 54b is connected at 55 to an air hose 56 (FIG. 6) leading to the holder assembly from the output side of the laminar flow regulator 28 in FIG. 1.

The jet air passage 31a in holder 29a at the opposite side of the latter's recess 32a leads to the upper end of an outlet passage 57a (FIG. 7) whose lower end is connected to a hose 58a that leads to the pilot pressure inlet port 27 (FIG. 1) of the corresponding pilot-operated valve 25.

As shown in FIG. 7, the usual dental handpiece 52a has an annular peripheral band 59a near its lower end which has a snug sliding fit in the holder recess 32a and when seated therein blocks both jet air passages 30a and 31a. Accordingly, when the handpiece is seated in this recess in its holder, the outlet hose 58a does not receive pressurized air.

It will be understood that there are three pilot-operated valves 25, one for each holder 29a, 29b or 29c, for controlling individually the respective air supplies to the corresponding dental handpieces. However, the system needs only a single air compressor 20, a single pressure regulator 21, a single foot-operated valve 22, and a single laminar pressure regulator 28 for controlling all of these air supplies.

Each of the remaining two holders 29b and 29c in the holder assembly is essentially similar to the just-described holder 29a, and the detailed description will not be repeated for these holders. Elements of the holders 29b and 29c which correspond to those of the holder 29a are given the same reference numerals, but with a "b" or "c" suffix.

In the particular embodiment illustrated, the handpiece 52a is a low speed drill operated by an air turbine but having no water supply, whereas the remaining handpieces 52b and 52c are high speed drills, each having an air turbine and a water supply.

In addition to having an individual pilot-operated valve 25 for controlling the air supply to its air turbine, each of the high speed drills 52b and 52c also has a similar pilot-operated valve controlling its water supply. Also, the foot-operated valve 22 (FIG. 1) has, in addition to the air inlet and air outlet, a water inlet and a water outlet whose fluid communication is controlled by a foot pedal. The water outlet of this foot-operated valve is connected to the main water inlet 24 of the pilot-operated water valve for each high speed drill 52b or 52c. Each of these water supply valves has its pilot inlet port 27 connected to the outlet hose 58b or 58c from the respective holder 29b or 29c. Consequently, whenever a high speed drill 58b or 58c is removed from its holder, the corresponding pilot-operated water supply valve will be opened by the same pilot pressure as the corresponding pilot-operated air supply valve for that drill.

In the particular embodiment illustrated, the holders 29a, 29b and 29c provide air and water passages for connecting air and water hoses for the respective handpieces. This is more a matter of convenience than of necessity since these internal passages in the holders may be omitted without sacrificing the advantageous principles of operation of this invention.

As shown in FIG. 5, the holder 29a for the low speed drill 52a has a horizontal passage 60a connected to an inlet port 61a on the bottom of this holder which is connected to an air hose 62a (FIG. 6) leading from the main outlet port 26 of the pilot-operated air supply valve 25 in FIG. 1. The opposite end of passage 60a in the handpiece holder is connected to an outlet port 63a on the bottom of this holder, which is connected to an air hose 64a leading up to the air turbine in the corresponding dental handpiece 52a.

The hose 62a, passage 60a and hose 64a are merely the functional equivalent of the schematically illustrated line in FIG. 1 leading from the main outlet port 26 of the pilot-operated air supply valve 25 to the air turbine in the handpiece.

Figure 8:
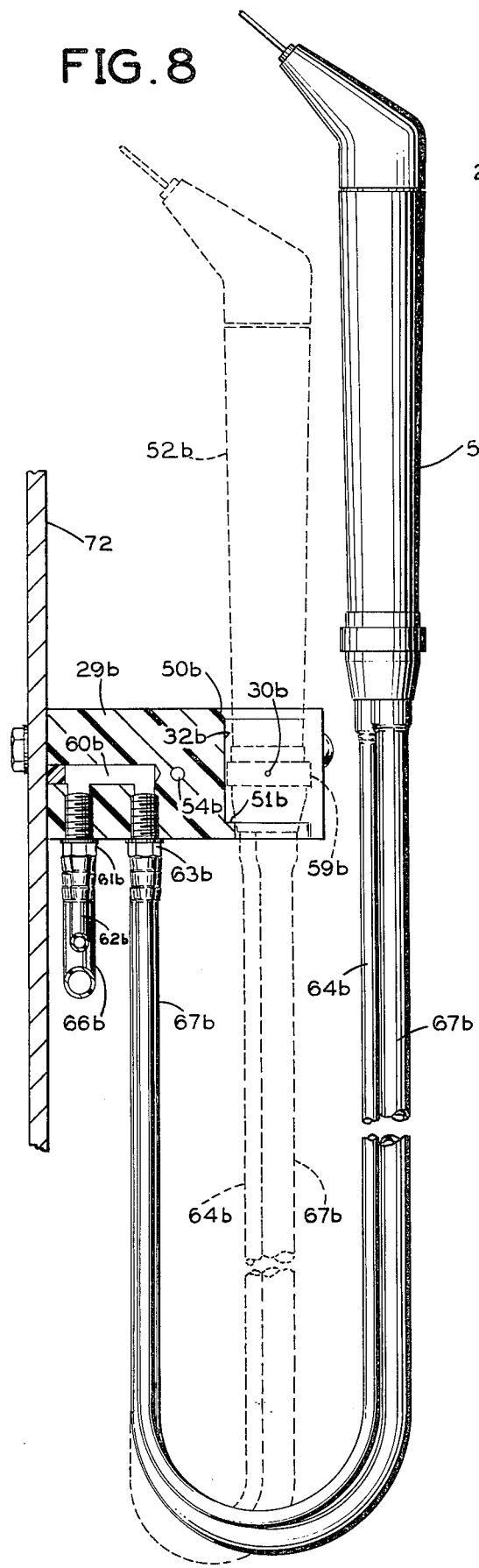
FIG. 8 is a vertical section taken along the line 8—8 in FIG. 6, with the handpiece shown in full lines removed from its holder and in phantom lines in the holder.

The next holder 29b in the assembly has a similar air passage 60b connecting air hoses 62b and 64b in the same fashion, as shown in detail in FIG. 8. In addition, holder 29b has a water passage 65b (FIG. 5) extending parallel to its air passage 60b connecting an inlet water hose 66b (FIG. 6) to an outlet water hose 67b. Hose 66b comes from the main outlet port 26 of the corresponding pilot-operated water supply valve 25. Hose 67b extends up to the high speed drill 52b.

Similar air and water passages 60c and 65c are provided in the final handpiece holder 29c for interconnecting corresponding air hoses 62c, 64c and water hoses 66c, 67c for the high speed drill 52c.

Referring to FIGS. 7 and 9, which show the high speed drill 52b and its holder 29b, when the drill is seated in the holder, as shown in phantom in FIG. 7, it blocks the air jet flow from passage 30b to passage 31b. However, when the drill is removed from the holder as shown in full lines in FIG. 8, the air jet flows from passage 30b (FIG. 9) across the holder recess 32b into passage 31b (assuming that the foot-operated air valve 22 is open). From passage 31b, the air jet pressure is applied via hose 58b to the pilot pressure inlet port 27 of the corresponding pilot-operated air supply valve 25, opening this valve as already described to permit air to flow from its main port 24 to its main outlet port 26 and from there through hose 62b, passage 60c in holder 29b, and hose 64b to the air turbine in this handpiece. Also, the pilot air pressure in hose 58b opens a pilot-operated water supply valve for this high speed drill, as already described.

Figure 6:
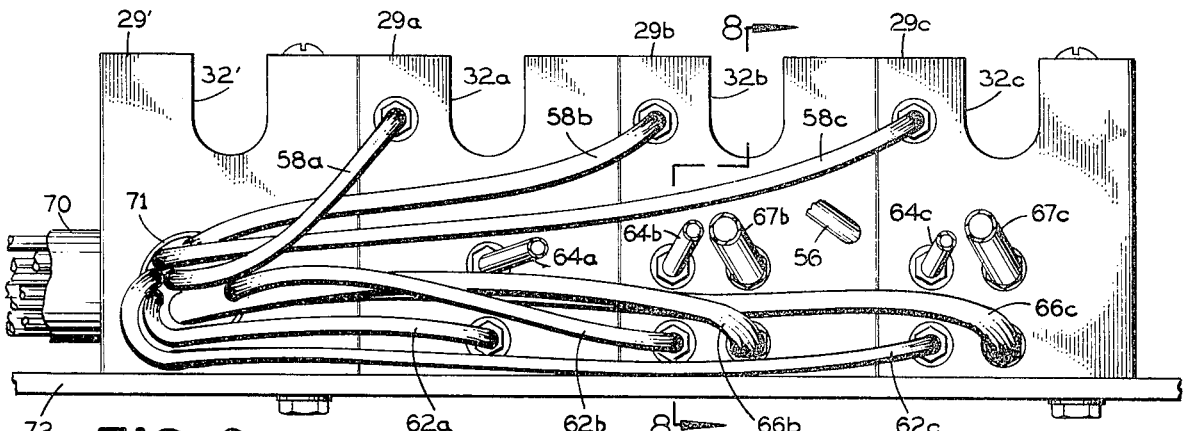
FIG. 6 is a bottom plan view of the handpiece holder of FIGS. 2-5.
Figure 7:
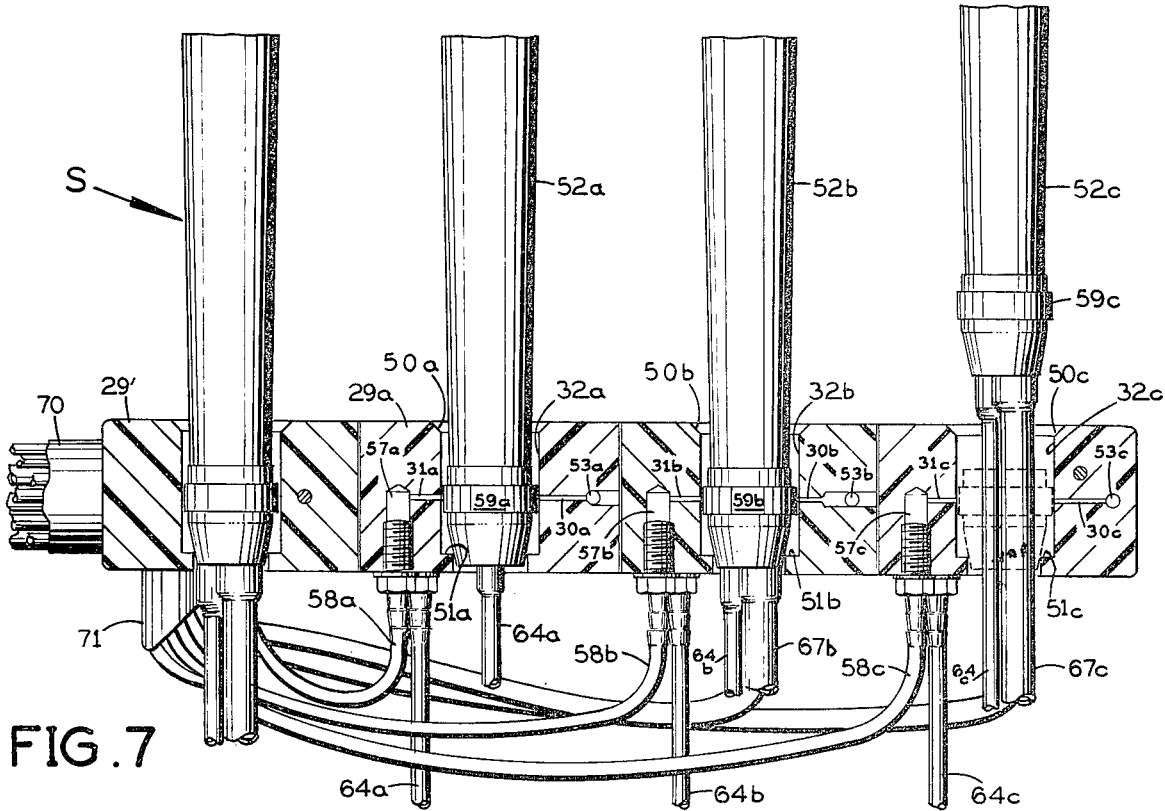
FIG. 7 is a longitudinal vertical section through this handpiece holder, taken along the line 7—7 in FIG. 4.

As shown in FIGS. 2, 5 and 6 the air hoses 56, 58a, 58b and 58c for the air jets, the main air inlet supply hoses 62a, 62b and 62c, and the water inlet supply hoses 66b and 66c all are clustered inside a sheath 70 which enters the holders 29' for the syringe at the left end of the holder assembly and makes a 90° turn therein and comes out through a fitting 71 on the bottom of this holder.

The four individual holders 29', 29a, 29b and 29c are bolted to a rigid support plate 72 at the back, as shown in FIGS. 5 and 6, so that they are juxtaposed side-by-side in the position shown in FIG. 5.

If one of the high speed drills is replaced by an ultrasonic scaler, the system would include an air pressure-operated switch downstream from the pilot-operated air supply valve 25 for the sealer. This switch is normally open, and it is closed in response to the opening of this air supply valve and the foot-operated air valve. When closed, this pressure switch turns on the ultrasonic scaler in a known manner.

FIGS. 10-14 show a modified arrangement in which the respective pilot-operated valves for the individual handpieces are integrated into the holder assembly. The operation of the apparatus, and particularly the manner in which the dental handpieces control the operation of the respective pilot-operated valves, is the same as already described in detail with reference to FIGS. 1-9 and this detailed description of the operation will not be repeated.

The holder assembly shown in FIG. 10 accommodates five handpieces, namely a syringe in recess 79', a low speed drill in recess 79a, and high speed drills in recesses 79b, 79c and 79d.

A pilot-operated air supply valve 80a is associated with handpiece recess 79a to control the supply of pressurized air to the air turbine in the low speed drill.

A pilot-operated air supply valve 80b and a similar pilot-operated water supply valve 81b are associated with handpiece recess 79b to control the respective supplies of air and water to the high speed drill which is seated in this recess when not in use. Similar air and water valves 80c and 81c are associated with recess 79c and similar valves 80d and 81d are associated with recess 80d.

As shown in FIG. 13, the handpiece holder assembly is of three-piece construction, including a back plate 82, and bottom and top pieces 83 and 84 bolted to the front of the back plate, with the top piece 84 directly overlying the bottom piece 83.

The back plate 82 is formed in its front face with a longitudinally extending air supply groove or channel 85 (FIGS. 11 and 14) and branch channels 86a, 86b, 86c and 86d extending from channel 85. As shown in FIG. 12, the branch air channel 86c leads to the main air inlet port at 87c of the pilot-operated valve 80c which is associated with the handpiece-receiving recess 79c. A flat annular washer 88c of rubber-like material is engaged between the end of this valve and the front face of the back plate 82 to provide a fluid-tight seal around the main air inlet at 87c. The other branch air channels 86a, 86b and 86d similarly lead to the respective main air inlets of the corresponding pilot-operated air supply valves 80a, 80b and 80d. The back plate 82 has an air inlet port 89 (FIGS. 11, 13 and 14) leading into channel 85. Port 89 receives pressurized air from a hose 90 (FIGS. 10 and 13) connected to the air outlet of the foot-operated valve 22 in FIG. 1.

The back plate 82 is formed in its front face with a similar longitudinally extending water supply channel 96 (FIGS. 11 and 14) and three branch water channels 96b, 96c and 96d which lead respectively to the main inlet ports of the pilot-operated water supply valves 81b, 81c and 81d. As shown in FIG. 10, a flat annular washer 98d of rubber-like material is sealingly engaged between the water supply valve 81d and the front face of the back plate 82 around the water inlet port at 97d of this valve. A similar arrangement is provided at each of the other water supply valves 81b 81c. The back plate has a water inlet port 99, leading into channel 95, to which a water supply hose H (FIG. 13) is connected. This hose is connected at its opposite end to the water outlet of the foot-pedal operated valve, as already described.

As shown in FIG. 10, O-ring seals 100a, 100b, 100c, and 100d, respectively, are provided at the front of the air supply valves 80a, 80b, 80c and 80d around the pilot pressure inlet ports for those valves. Similar O-ring seals 101b, 101c and 101d are provided around the pilot pressure inlet ports of the water supply valves 81b, 81c and 81d, respectively. The bottom and top pieces 83, 84 of the handpiece holder define between them respective individual annular chambers 102a, 102b, 102c and 102d which receive the air supply valves and which are sealed in fluid-tight fashion at each end by the corresponding annular washer and O-ring seal, respectively. Similar sealed chambers 103b, 103c and 103d are provided for the individual water supply valves 81b, 81c and 81d, respectively. Each of these chambers is larger in cross-section than the corresponding valve so that an annular space is provided between them.

As shown in FIG. 10, the air supply valve 80d has a main air outlet port 104d which opens into chamber 102d. At the back of the holder, an outlet port 105d connects chamber 102d to an air hose leading to the air turbine for the high speed drill that normally is seated in the holder recess 79c.

Each of the other air and water supply valves has a similar main outlet port and each of the other valve-receiving chambers has an outlet port at the back which is connected to a corresponding air hose or water hose for the corresponding handpiece. FIG. 5 shows the air outlet hose 106c for air supply valve 80c.

The abutting inner faces of the bottom and top pieces 83, 84 of the handpiece holder are formed with aligned, narrow, shallow grooves which define between them a first pilot air passageway 107 (FIG. 10). The back end of this passageway is connected to a first pilot air inlet port 108 in the back plate 102 of the holder. A pilot air inlet hose 109 is connected at one end to this inlet port and at its opposite end to the air outlet of a foot pedal-operated valve as shown at 22 in FIG. 1.

The front end of pilot air passageway 107 is connected to a branch passage 110d, which opens into the handpiece recess 79d at one side. A similar, aligned passage 111d is open at the opposite side of this recess to receive a jet of air from passage 110d when the corresponding handpiece is removed from this recess and the foot pedal-operated valve is opened. Passage 111d is connected to a pilot pressure inlet port at 112d for the air supply valve 80d and to a pilot pressure inlet port at 113d for the water supply valve 81d.

The front end of pilot air passageway 107 also is connected to a branch passage 110c, which opens into the handpiece recess 79c at one side. A similar, aligned passage 111c on the opposite side of this recess is connected to pilot pressure inlet ports at 112c and 113c for the air and water supply valves 80c and 81c, respectively.

A similar second pilot air passageway 117 in the holder is connected at its back end to a second pilot air inlet port 118 in the back plate, to which a second pilot air inlet hose 119 is connected at one end. The opposite end of hose 119 is connected to the air outlet of the foot pedal-operated valve 22.

The front end of pilot air passageway 117 is connected to branch passages 120a and 120b, respectively, each leading to one side of the corresponding handpiece-receiving recess 79a or 79b in the holder.

A pilot air passage 121a on the opposite side of recess 79a (in alignment with passage 120a) leads to a pilot pressure inlet port at 122a for the air supply valve 80a.

A pilot air passage 121b on the opposite side of recess 79b (in alignment with passage 120b) leads to a pilot pressure inlet port at 122b for the air supply valve 80b and to a pilot pressure inlet port at 123b for the water supply valve 81b.

In the operation of this apparatus, whenever the foot pedal for valve 22 (FIG. 1) is depressed, pressurized air is supplied to the air hose 90 leading into the main air channel 85 in the holder and is supplied to the pilot air hoses 109 and 119 leading into the pilot air passageways 107 and 117 in the holder, and water is supplied to the hose H leading into the water channel 95 in the holder.

Whenever anyone of the handpieces is removed from the corresponding recess 79a, 79b, 79c or 79d in the holder, a jet of air flows across that recess from the respective passage 120a, 120b, 110c or 110d into the corresponding opposite passage 121a, 121b, 111c or 111d to open the corresponding air supply valve or pair of air and water supply valves 80a, 80b–80b, 80c–81c, or 80d–81d to supply air or both air and water to that handpiece.

Either the apparatus of FIGS. 2–9 or that of FIGS. 10–14 may be used without the usual foot-operated valve 22 for air, in which case the air supply would be controlled only by the position of the handpiece with respect to its holder and not jointly by the latter and the foot-operated air valve. However, it is believed that most dentists will prefer the joint control system because they have become accustomed to using the foot-operated valves.

FIGS. 15–18 show a third embodiment of the present invention in the form of a handpiece holder on which the dental handpiece rests horizontally when not in use.

This holder has a two-piece housing comprising a bottom piece 130, with a generally flat bottom and upstanding sides, and a top cover 131. The top cover has yoke-shaped supports 132 and 133 on the top near each end, each presenting an upwardly-facing semi-circular recess in which the handpiece 134 is cradled.

The housing has an air inlet port 135 (FIG. 16) at one end to which is attached a hose 136 leading from a pressure regulator as shown at 21 in FIG. 1, which passes pressure-regulated air from an air compressor.

A first branch passage 137 (FIG. 16) extends from the inlet port 135 to the main inlet port 138 of a pilot-operated air supply valve 139 of the type shown in FIG. 3. This valve has its main outlet port 140 connected to a hose 141 leading to the air turbine in the dental handpiece 134. This valve also has a pilot pressure inlet port 142.

The circuit leading to this pilot pressure port 142 includes, in series (FIG. 16), a second branch passage 143 connected to the inlet port 135, a manually adjustable laminar air flow regulator 144, a manually-operated on/off valve 145, and a valve 146 operated mechanically by the dental handpiece 134.

Figure 16:
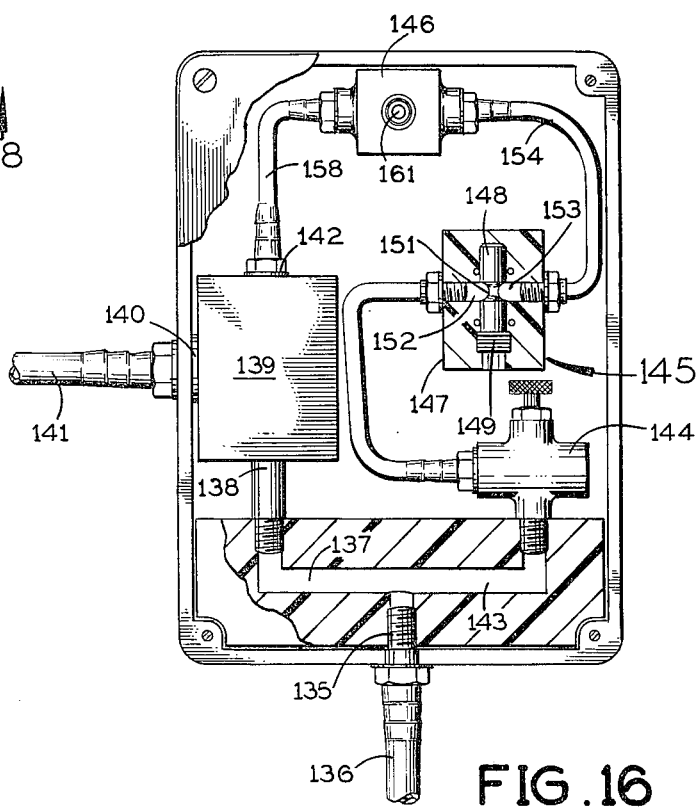
FIG. 16 is a top plan view of the FIG. 15 holder with its top cover broken away for clarity.
Figure 17:
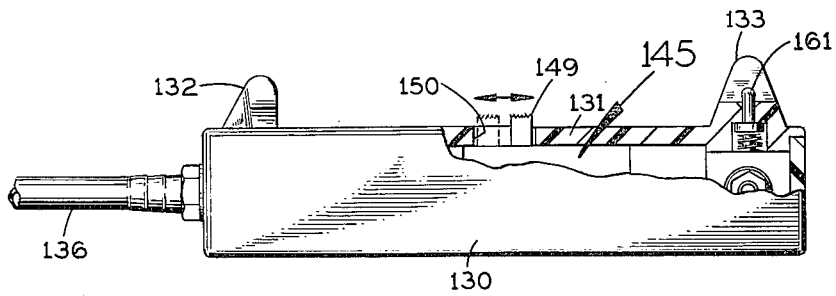
FIG. 17 is an end elevational view of this holder, with parts broken away for clarity.

The on/off valve 145 may be of any appropriate design. As shown in FIG. 16, it comprises a valve body 147 in which a valve spool 148 is slidably reciprocable. This spool is connected to a finger knob 149 (FIG. 17) which projects up through a slot 150 in the top cover 131 of the housing. The valve spool 148 has an annular groove 151 in its periphery about midway along its its length (FIG. 16), which provides fluid communication between an inlet port 152 and an outlet port 153 on opposite sides of the valve spool 148 when this valve spool is shifted to the "on" position. When the valve spool 148 is displaced downward in FIG. 16 from this position, the groove 151 in the valve spool is out of registration with the inlet and outlet ports 152, 153 and the valve spool blocks the flow of air between these ports.

The outlet port 153 of the on/off valve 145 is connected through a short hose or tube 154 (FIG. 16) to an inlet passage 155 (FIG. 18) in valve 146. The inner end of this passage is normally blocked by a valve member, which is the lower end of a vertically reciprocable plunger or pin 156. On the opposite side of this plunger an outlet passage 157 leads to a hose or tube 158 that is connected to the pilot pressure inlet 142 on the pilot-operated air supply valve 139.

The plunger 156 carries an enlarged transverse segment 159 intermediate its ends, and a coil spring 160 acts against this head to bias the plunger upward to a position in which its lower end would unblock the inlet and outlet passages 155 and 157. Above this enlarged segment 159 the plunger projects up slidably through a vertical bore 161 in the top cover which leads up into the handpiece-receiving recess in yoke 133.

Figure 18:
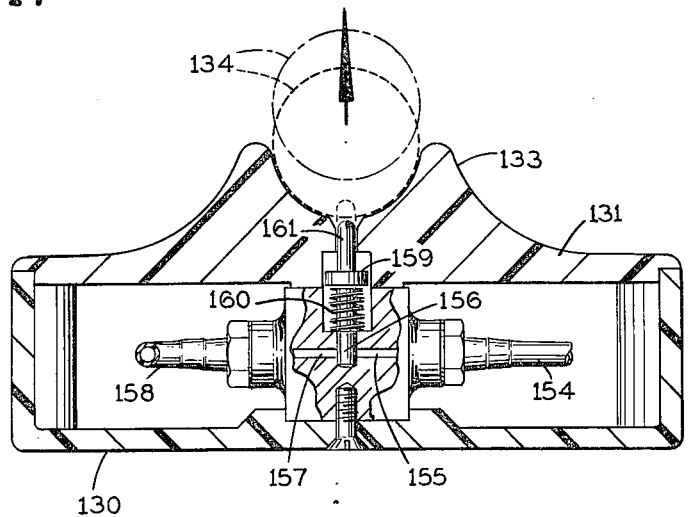
FIG. 18 is a vertical cross-section taken along the line 18—18 in FIG. 15 and showing the mechanically-operated pilot air valve whose operation depends on whether the dental handpiece is in or out of the holder.

When the handpiece 134 is seated in the yokes 132 and 133, it holds the plunger 156 down in the position shown in FIG. 18, closing valve 146 so that there is no appreciable flow of air between its aligned passages 155 and 157.

When the handpiece is removed from the holder, spring 160 forces the plunger 156 up to a valve-opening position in which air is free to flow from inlet passage 155 to outlet passage 157. This air pressure is applied to the pilot pressure port at 142 (FIG. 16) to open the air supply valve 139.

I claim:

1. In a dental apparatus for use with a dental handpiece supplied with pressure fluid, said apparatus including a pilot-operated valve having:
   a main inlet for receiving pressure fluid;
   a main outlet for passing the pressure fluid from said main inlet to the handpiece;
   normally-closed valve means between said main inlet and said main outlet normally blocking the flow of pressure fluid between them;
   a pilot pressure inlet;
   and means for opening said valve means to connect said main inlet to said main outlet in response to pilot pressure at said pilot pressure inlet; the improvement which comprises:
   a holder for the handpiece having means defining a pair of aligned small passages, one for receiving pressure fluid and the other connected to said pilot pressure inlet of said pilot-operated valve for applying pilot pressure thereto;

and means for blocking the flow of pressure fluid from said one passage to said other passage when the handpiece is in the holder and for passing pressure fluid from said one passage to said other passage when the handpiece is out of the holder;

said holder having a recess for receiving said handpiece, and said passages opening into said recess on opposite sides of the latter and in alignment with each other;

and said last-mentioned means comprising the dental handpiece itself which, when received in said recess, blocks said passages.

2. A dental apparatus according to claim 1, wherein said recess is open at the top, bottom and front, and said passages are aligned horizontally on opposite sides of said recess.

3. A dental apparatus according to claim 1, wherein the distance across said recess between said passages is not more than substantially 20 times the diameter of the passages.

4. A dental apparatus according to claim 3, wherein the pressure fluid applied to said one passage is air.

5. A dental apparatus according to claim 4, wherein the pressure fluid supplied to the dental handpiece is air.

6. A dental apparatus according to claim 4, wherein the pressure fluid supplied to the dental handpiece is water.

7. A dental apparatus according to claim 3, wherein the pressure of the air applied to said one passage is substantially 0.5 pound per square inch, the diameter of said passages on opposite sides of said recess is within the range from substantially 0.0035 to 0.0040 inch, and the distance across said recess between said passages is substantially 0.656 inch.

8. A dental apparatus according to claim 1, wherein said pilot-operated valve is spaced from said holder, and further comprising a hose connecting said other passage in the holder to said pilot pressure inlet of the pilot-operated valve.

9. A dental apparatus according to claim 1, wherein said pilot-operated valve is positioned in said holder, and said holder has an internal passageway connecting said other passage to said pilot pressure inlet of the pilot-operated valve.

10. In a dental apparatus for use with a dental handpiece supplied with pressure fluid, said apparatus including a pilot-operated valve having:
a main inlet for receiving pressure fluid;
a main outlet for passing the pressure fluid from said main inlet to the handpiece;
normally-closed valve means between said main inlet and said main outlet normally blocking the flow of pressure fluid between them;
a pilot pressure inlet;
and means for opening said valve means to connect said main inlet to said main outlet in response to pilot pressure at said pilot pressure inlet;
the improvement which comprises:
a holder for the handpiece having means defining a pair of aligned small passages, one for receiving pressure fluid and the other connected to said pilot pressure inlet of said pilot-operated valve for applying pilot pressure thereto;
and means for blocking the flow of pressure fluid from said one passage to said other passage when the handpiece is in the holder and for passing pressure fluid from said one passage to said other passage when the handpiece is out of the holder;
said last-mentioned means comprising a normally-open valve member controlling the flow of pressure fluid between said passages and constructed and arranged to be closed when the dental handpiece is in said holder;
and said holder presenting a generally U-shaped recess for receiving the dental handpiece, and said normally-open valve member having an operator biased into said recess and engageable thereat by the handpiece to be displaced by the latter to a closed position.

11. A dental apparatus according to claim 10, wherein said holder has an air inlet and an air outlet and contains said pilot-operated valve, a manually-operated on/off valve connected between said air inlet and said one passage, an adjustable flow regulator connected between said air inlet and said on/off valve, conduit means connecting said air inlet of the holder to said main inlet of said pilot-operated valve, and conduit means connecting said other passage to the pilot pressure inlet of said pilot-operated valve, and wherein said main outlet of said pilot-operated valve is connected to said air outlet of the holder.

12. A dental apparatus according to claim 11, wherein said recess is at the top of said holder, and said operator is spring-biased up into said recess to a position uncovering said passages and is depressable by the handpiece, when the latter is seated in the recess, to a position blocking said passages.

13. In a dental apparatus for use with a dental handpiece supplied with pressure fluid, said apparatus including a pilot-operated valve having:
a main inlet for receiving pressure fluid;
a main outlet for passing the pressure fluid from said main inlet to the handpiece;
means including pressure regulator means for supplying pressure fluid to said main inlet;
normally-closed valve means between said main inlet and said main outlet normally blocking the flow of pressure fluid between them;
a pilot pressure inlet;
and means for opening said valve means to connect said main inlet to said main outlet in response to pilot pressure at said pilot pressure inlet;
the improvement which comprises:
a holder for the handpiece having means defining a pair of aligned small passages, one for receiving pressure fluid and the other connected to said pilot pressure inlet of said pilot-operated valve for applying pilot pressure thereto;
laminar regulator means connected to said pressure regulator means and said one passage for supplying regulated pressure fluid to said one passage;
and means for blocking the flow of pressure fluid from said one passage to said other passage when the handpiece is in the holder and for passing pressure fluid from said one passage to said other passage when the handpiece is out of the holder.

14. A fluidic drive dental system for effecting fluidic driving of a dental handpiece comprising in combination a manually actuatable valve means for selectively producing a first fluidic pressure in response to the manual actuation thereof, handpiece control valve means including a support means for supporting a dental handpiece so that said control valve means is selectively acutated in response to said dental handpiece being removed from said support means, said control valve means being fluidically coupled intermediate said manually actuatable valve means and said dental handpiece for applying said first fluidic pressure produced by said manually actuated valve means to said dental handpiece to effect operation thereof in response to a coincidental actuation of said manually actuatable valve means and said handpiece control valve means.

15. A fluidic drive dental system as claimed in claim 14, wherein said handpiece control valve means is adapted to produce a second fluidic pressure in response to the selective actuation thereof, said handpiece control valve means further including pilot valve means disposed intermediate said manually actuated valve means and said dental handpiece means, said pilot valve means being fluidically coupled to said manually actuatable valve means for applying the first fluidic pressure produced thereby to said dental handpiece to effect fluidic driving thereof in response to said second fluidic pressure produced by said handpiece control valve means being coincidentally applied thereto.

16. A fluidic drive dental system as claimed in claim 15, wherein said manually actuatable valve means includes a foot operated means for determining the force of said first fluidic operating pressure produced thereby.

17. A fluidic drive dental system as claimed in claim 15, and including fluidic pressure means for generating a predetermined fluidic pressure, said manually actuatable valve means and said handpiece control valve means being fluidically coupled to said fluidic pressure means for receiving said predetermined fluidic pressure and in response thereto respectively producing said respective first and second fluidic pressures.

18. A fluidic drive dental system as claimed in claim 16, and including fluidic pressure means for generating a predetermined fluidic pressure, said manually actuatable valve means being coupled to said fluidic pressure means and in response to said predetermined fluidic pressure being applied thereto being adapted to produce said first fluidic pressure and being further adapted to apply to said handpiece control valve means said second fluidic pressure.

19. A fluidic drive dental system as claimed in claim 15, wherein said support means include a pair of aligned, spaced-apart fluidic passages, said first aligned fluidic passage being coupled to said first valve means for receiving said second fluidic pressure produced thereby and said other fluidic passage being fluidically coupled to said pilot valve means and being selectively disposable into fluid communication with said first passage to thereby apply said second fluidic pressure to said pilot valve means in response to said dental handpiece being removed from said support means.

20. A fluidic drive dental system as claimed in claim 19, wherein said support means forms a recess for holding a dental handpiece, said fluidic passages being spaced apart on opposite sides of said recess so that said pair of passages are normally out of fluid communication with each other when a dental handpiece is held in said recess.

21. A fluidic drive dental system as claimed in claim 19, wherein said support means includes displacement means adapted to be displaced between said pair of fluidic passages and thereby prevent fluidic pressure from being applied to said pilot valve means in response to the dental handpiece being supported by said support means.

22. A fluidic drive dental system for effecting fluidic operation of a dental handpiece comprising in combination, fluidic pressure means for generating a predetermined fluidic pressure, and manually actuatable first valve means fluidically coupled to said fluidic pressure means for producing a first operating pressure for operating said dental handpiece and for producing a second fluidic pressure for gating said first operating fluidic pressure to said dental handpiece to effect fluidic operation of same, pilot valve means for selectively fluidically applying said first fluidic operating pressure to said dental handpiece in response to said second fluidic gating pressure being selectively applied thereto, and a normally closed manually actuatable second valve means fluidically coupled to said first valve means and said pilot valve means, for receiving said second fluidic pressure produced by said first valve means and for applying said second fluidic pressure to said pilot valve means in response to said second valve means being selectively opened.

23. A fluidic drive dental system as claimed in claim 22, wherein said second valve means includes holder means for supporting said dental handpiece so that second valve means remains normally closed when said holder means is holding a dental handpiece and is selectively open in response to the dental handpiece being removed from the holder means.

24. A fluidic drive dental system as claimed in claim 23, wherein said first valve means includes a foot operated means for determining the force of the first fluidic operating pressure produced thereby.

25. A fluidic drive dental system as claimed in claim 24, and including laminar regulating means disposed intermediate said first valve means and said second valve means for regulating the laminar flow of said second fluidic pressure.

26. A fluidic drive dental system as claimed in claim 22, wherein said second valve means includes a pair of aligned, spaced-apart fluidic passages, said first aligned fluidic passage being coupled to said first valve means for receiving said second fluidic pressure produced thereby and said other fluidic passage being fluidically coupled to said pilot valve means and being selectively disposable into fluid communication with said first passage to thereby apply said second fluidic pressure to said pilot valve means.

27. A fluidic drive dental system as claimed in claim 26, wherein said holder means forms a recess for receiving a dental handpiece, said fluidic passages being spaced apart on opposite sides of said recess so that said pair of passages are normally out of fluid communication with each other when a dental handpiece is disposed in said recess.

28. A fluidic drive dental systems as claimed in claim 27 wherein said recess is opened at the top, bottom and front, and said first and second passages are aligned horizontally on opposite sides of said recess.

29. A fluidic drive dental system as claimed in claim 27, wherein the distance across said recess between said spaced apart fluidic passages is not more than substantially twenty (20) times the diameter of the fluidic passages.

30. A fluidic drive dental system as claimed in claim 26, wherein said holder means includes displacement means adapted to be displaced between said pair of fluidic passages to thereby prevent fluidic pressure from being applied to said pilot valve means in response to a dental handpiece being held by said holder means.

31. A fluidic drive dental system as claimed in claim 26, wherein each of said respective fluidic pressures are pneumatic.

32. A fluidic drive dental system as claimed in claim 26, wherein each of said respective fluidic pressures are hydraulic.

* * * * *